(12) United States Patent
Amano

(10) Patent No.: US 10,780,000 B2
(45) Date of Patent: Sep. 22, 2020

(54) ABSORBENT ARTICLE HAVING LAMINATED SECOND SHEET WITH THROUGH-HOLES

(71) Applicant: LIVEDO CORPORATION, Shikokuchuo-shi, Ehime (JP)

(72) Inventor: Emi Amano, Mima-gun (JP)

(73) Assignee: LIVEDO CORPORATION, Shikokuchuo, Ehime (JP)

( * ) Notice: Subject to any disclaimer, the term of this patent is extended or adjusted under 35 U.S.C. 154(b) by 662 days.

(21) Appl. No.: 15/317,185

(22) PCT Filed: Jun. 23, 2015

(86) PCT No.: PCT/JP2015/068047
§ 371 (c)(1),
(2) Date: Dec. 8, 2016

(87) PCT Pub. No.: WO2016/009795
PCT Pub. Date: Jan. 21, 2016

(65) Prior Publication Data
US 2017/0112688 A1    Apr. 27, 2017

(30) Foreign Application Priority Data
Jul. 14, 2014  (JP) .................................. 2014-144278

(51) Int. Cl.
*A61F 13/15*    (2006.01)
*A61F 13/20*    (2006.01)
(Continued)

(52) U.S. Cl.
CPC ........ *A61F 13/53747* (2013.01); *A61F 13/49* (2013.01); *A61F 13/511* (2013.01);
(Continued)

(58) Field of Classification Search
CPC ...... A61F 13/49; A61F 13/511; A61F 13/537; A61F 13/53747; A61F 13/539;
(Continued)

(56) References Cited

U.S. PATENT DOCUMENTS 5,516,572 A    5/1996  Roe
5,591,149 A *  1/1997  Cree .................. A61F 13/47218
                                                            604/368
(Continued)

FOREIGN PATENT DOCUMENTS

CN    1115343 A    1/1996
CN    1146219 A    3/1997
(Continued)

OTHER PUBLICATIONS

Office Action dated May 8, 2018, issued in counterpart Japanese application No. 2014-144278, with English translation. (6 pages).
(Continued)

*Primary Examiner* — Michele M Kidwell
(74) *Attorney, Agent, or Firm* — Westerman, Hattori, Daniels & Adrian, LLP

(57) ABSTRACT

An absorbent article (1) comprising a top sheet (2), a back sheet (3), an absorbent body (4) disposed therebetween and a second sheet (10) disposed between the top sheet (2) and the absorbent body (4), wherein the second sheet (10) is composed of a laminate having a nonwoven fabric layer (11) and a plastic film layer (12) from the top sheet side and has a plurality of through-holes (13).

17 Claims, 3 Drawing Sheets

(51) Int. Cl.
*A61F 13/537* (2006.01)
*A61F 13/49* (2006.01)
*A61F 13/511* (2006.01)
*A61F 13/539* (2006.01)
*A61F 13/53* (2006.01)

(52) U.S. Cl.
CPC .......... *A61F 13/537* (2013.01); *A61F 13/539* (2013.01); *A61F 2013/530145* (2013.01); *A61F 2013/53782* (2013.01); *A61F 2013/53908* (2013.01)

(58) Field of Classification Search
CPC .......... A61F 2013/530145; A61F 2013/53782; A61F 2013/53908
See application file for complete search history.

(56) References Cited

U.S. PATENT DOCUMENTS

| | | | |
|---|---|---|---|
| 5,603,707 A * | 2/1997 | Trombetta | A61F 13/53743 604/383 |
| 5,733,628 A | 3/1998 | Pelkie | |
| 6,231,555 B1 * | 5/2001 | Lynard | A61F 13/5126 604/364 |
| 6,303,208 B1 | 10/2001 | Pelkie | |
| 6,849,319 B2 | 2/2005 | Cree et al. | |
| 7,607,711 B2 * | 10/2009 | Marshall | B62D 33/0273 296/51 |
| 7,956,236 B2 * | 6/2011 | Ponomarenko | A61F 13/495 604/378 |
| 8,227,660 B2 * | 7/2012 | Hara | A61F 13/15203 604/380 |
| 8,722,173 B2 | 5/2014 | Oba et al. | |
| 9,173,782 B2 * | 11/2015 | Takken | A61F 13/51104 |
| 9,744,080 B2 * | 8/2017 | Lee | A61F 13/15203 |
| 2001/0027302 A1 * | 10/2001 | Glaug | A61F 13/53747 604/378 |
| 2002/0022812 A1 * | 2/2002 | Kasai | A61L 15/34 604/364 |
| 2002/0065009 A1 | 5/2002 | Pelkie | |
| 2003/0097101 A1 * | 5/2003 | Schmidt | A61F 13/5376 604/367 |
| 2003/0120249 A1 * | 6/2003 | Wulz | A61F 13/4702 604/385.101 |
| 2003/0124311 A1 | 7/2003 | Cree et al. | |
| 2005/0049567 A1 * | 3/2005 | Cree | A61F 13/15203 604/378 |
| 2005/0164705 A1 * | 7/2005 | Rajkotia | H04W 68/00 455/436 |
| 2008/0206529 A1 * | 8/2008 | Ueminami | A61F 13/512 428/196 |
| 2008/0294135 A1 * | 11/2008 | Hara | A61F 13/15203 604/367 |
| 2009/0026651 A1 * | 1/2009 | Lee | B29C 48/14 264/156 |
| 2011/0160687 A1 * | 6/2011 | Welch | B32B 37/153 604/367 |
| 2012/0045620 A1 | 2/2012 | Oba et al. | |
| 2012/0164908 A1 | 6/2012 | Kunimoto | |
| 2014/0296815 A1 * | 10/2014 | Takken | A61F 13/512 604/383 |
| 2015/0164705 A1 * | 6/2015 | Thomas | A61F 13/15593 428/172 |
| 2015/0283003 A1 * | 10/2015 | Rosati | A61F 13/5126 206/526 |
| 2016/0129626 A1 * | 5/2016 | Arora | A61F 13/511 264/40.1 |
| 2016/0213531 A1 * | 7/2016 | Takahashi | B32B 5/26 |

FOREIGN PATENT DOCUMENTS

| | | | |
|---|---|---|---|
| CN | 1188638 | A | 7/1998 |
| CN | 1599585 | A | 3/2005 |
| CN | 1617696 | A | 5/2005 |
| CN | 1964685 | A | 5/2007 |
| CN | 102471967 | A | 5/2012 |
| CN | 102482817 | A | 5/2012 |
| GB | 2288412 | A | 10/1995 |
| JP | 52-42916 | A | 4/1977 |
| JP | 2000-140015 | A | 5/2000 |
| JP | 2005-348937 | A | 12/2005 |
| JP | 2007-167212 | A | 7/2007 |
| JP | 2008-113857 | A | 5/2008 |
| JP | 2009-6717 | A | 1/2009 |
| JP | 2011-55959 | A | 3/2011 |
| JP | 2012-5744 | A | 1/2012 |
| JP | 2012-157595 | A | 8/2012 |
| JP | 2012157595 | A | 8/2012 |
| JP | 2013-230408 | A | 11/2013 |
| WO | 00/59430 | * | 10/2000 .......... A61F 13/15 |
| WO | 2011/016343 | A1 | 2/2011 |

OTHER PUBLICATIONS

International Search Report dated Sep. 8, 2015, issued in counterpart application No. PCT/JP2015/068047. (2 pages).
Office Action, dated Jul. 2, 2019, issued in counterpart Chinese Application No. 201580033810.X (w/ English translation; 20 pages).
Office Action, dated May 11, 2020, issued in counterpart Chinese Application No. 201580033810.X (w/ English translation; 19 pages).
Office Action, dated Jan. 3, 2020, issued in counterpart Chinese Application No. 201580033810.X (w/ English translation; 19 pages).

* cited by examiner

ABSORBENT ARTICLE HAVING LAMINATED SECOND SHEET WITH THROUGH-HOLES

TECHNICAL FIELD

The present invention relates to an absorbent article such as a disposable diaper, an incontinence pad (including a light incontinence pad) and a sanitary napkin.

BACKGROUND ART

Conventionally, an absorbent article comprising a top sheet, a back sheet and an absorbent body disposed therebetween, wherein a second sheet is disposed between the top sheet and the absorbent body, is known. The second sheet is provided for improving an absorbing property of urine and the like in the absorbent article; and for example, Patent Literature 1 discloses an absorbent article provided with a second sheet that is composed of a nonwoven fabric which surface is given uneven configurations, Patent Literature 2 discloses an absorbent article provided with a second sheet that is composed of a nonwoven fabric formed from hallow fibers, Patent Literature 3 discloses an absorbent article provided with a second sheet that is composed of a nonwoven fabric formed from synthetic fibers and having a two-layer structure of a low density layer on the top sheet side and a high density layer on the absorbent body side, and Patent Literature 4 discloses an absorbent article provided with a second sheet that is composed of a plastic film in which multiple holes whose side wall projects toward a back sheet side from a top sheet side are formed.

CITATION LIST

Patent Literature

Patent Literature 1
  Japanese Unexamined Laid-open Patent Application Publication No. 2000-140015
Patent Literature 2
  Japanese Unexamined Laid-open Patent Application Publication No. 2011-55959
Patent Literature 3
  Japanese Unexamined Laid-open Patent Application Publication No. 2008-113857
Patent Literature 4
  Japanese Unexamined Laid-open Patent Application Publication No. 2012-5744

SUMMARY OF INVENTION

Technical Problem

As described above, various second sheets have been proposed heretofore, and a second sheet which is capable of further improving performance of the absorbent article is required. The present invention has been achieved in view of the above circumstances, and the object of the present invention is to provide an absorbent article provided with a second sheet that is excellent in absorbing performance of urine and the like and is capable of reducing wettability of the top sheet.

Solution to Problem

An absorbent article of the present invention which solves the above problems comprises a top sheet, a back sheet, an absorbent body disposed therebetween and a second sheet disposed between the top sheet and the absorbent body, wherein the second sheet is composed of a laminate having a nonwoven fabric layer and a plastic film layer from the top sheet side and has a plurality of through-holes. In the absorbent article of the present invention, since the second sheet formed in the above manner is disposed between the top sheet and the absorbent body, urine and the like absorbed by the top sheet is rapidly drawn into the second sheet and urine and the like which has reached the second sheet further transfers to the absorbent body through the through-holes. Meanwhile, urine and the like which has reached the absorbent body is prevented from returning to the top sheet side by the presence of the plastic film layer. Therefore, the absorbent article of the present invention is excellent in absorbing performance of urine and the like and is capable of reducing wettability of the top sheet, that improves a wearing feeling.

The nonwoven fabric layer is preferably made of a heat-embossed nonwoven fabric. When the nonwoven fabric constituting the nonwoven fabric layer is heat-embossed, volume of the nonwoven fabric layer is suppressed, whereby a remaining amount of urine and the like in the nonwoven fabric layer can be reduced, while ensuring a drawing effect of urine and the like by the nonwoven fabric layer. Therefore, the amount of urine and the like that returns to the top sheet from the second sheet is decreased, and wettability of the top sheet can be reduced.

It is preferred that each of the through-holes in the second sheet is larger than embossed parts formed by the heat-embossing. When the through-hole is formed larger than the embossed part, urine and the like easily moves to the through-hole without remaining at the embossed part and further easily moves to the absorbent body through the through-hole.

The second sheet is preferably formed such that the nonwoven fabric layer is intruded into the through-hole. When the through-hole is formed in this manner, urine and the like is likely to smoothly move to the through-holes from the nonwoven fabric layer smoothly. As a result, urine and the like easily moves to the absorbent body through the through-holes smoothly, whereby wettability of the top sheet can be further reduced.

It is preferred that a surface of the back sheet side of the second sheet projects toward the back sheet along an outer edge of the through-hole. When the second sheet is formed in this manner, urine and the like which has passed through the through-hole tends to smoothly move to the absorbent body by running down the part projecting toward the back sheet along the outer edge of the through-hole. As a result, wettability of the top sheet can be further reduced.

It is preferred that the nonwoven fabric layer is made of a short-fiber nonwoven fabric and the constituent fibers of the nonwoven fabric orient in the longitudinal direction of the absorbent article. When the nonwoven fabric layer is constituted in this manner, the effect of reducing wettability of the top sheet can be enhanced, and the whole of the absorbent body tends to contribute to the absorption of urine and the like effectively, since in the nonwoven fabric layer, urine and the like spreads more easily in the longitudinal direction than in the width direction of the absorbent article.

The nonwoven fabric layer and the plastic film layer are preferably joined to each other with an adhesive. Thereby, rupture strength of the plastic film layer is likely to be ensured as compared with, for example, the case where the nonwoven fabric layer and the plastic film layer are thermal-bonded to each other. In addition, the plastic film layer is prevented from heat-hardening and flexibility of the second sheet can be ensured.

It is preferred that the nonwoven fabric layer has a lower mass per a unit area than the top sheet. When the nonwoven fabric layer is formed to have a lower mass per a unit area than the top sheet, the returning amount can be suppressed even in the case where urine and the like remaining in the nonwoven fabric layer of the second sheet returns to the top sheet, whereby it becomes possible to maintain the top sheet relatively dry.

The top sheet is preferably made of a heat-embossed nonwoven fabric. When the top sheet is made of a heat-embossed nonwoven fabric, the top sheet is made relatively thin, and hence, urine and the like is likely to promptly pass through the top sheet and is less likely to remain in the top sheet. Therefore, it becomes possible to reduce wettability of the top sheet.

Advantageous Effects of Invention

Since the absorbent article of the present invention is provided with the second sheet which is composed of a laminate having a nonwoven fabric layer and a plastic film layer from the top sheet side and has a plurality of through-holes, urine and the like absorbed by the top sheet is rapidly drawn to the second sheet and is transferred to the absorbent body, while the urine and the like absorbed by the absorbent body is prevented from returning to the top sheet side. Therefore, the absorbent article of the present invention is excellent in absorbing performance of urine and the like and is capable of reducing wettability of the top sheet, that improves a wearing feeling.

DESCRIPTION OF THE PREFERRED EMBODIMENTS

Figure 1:
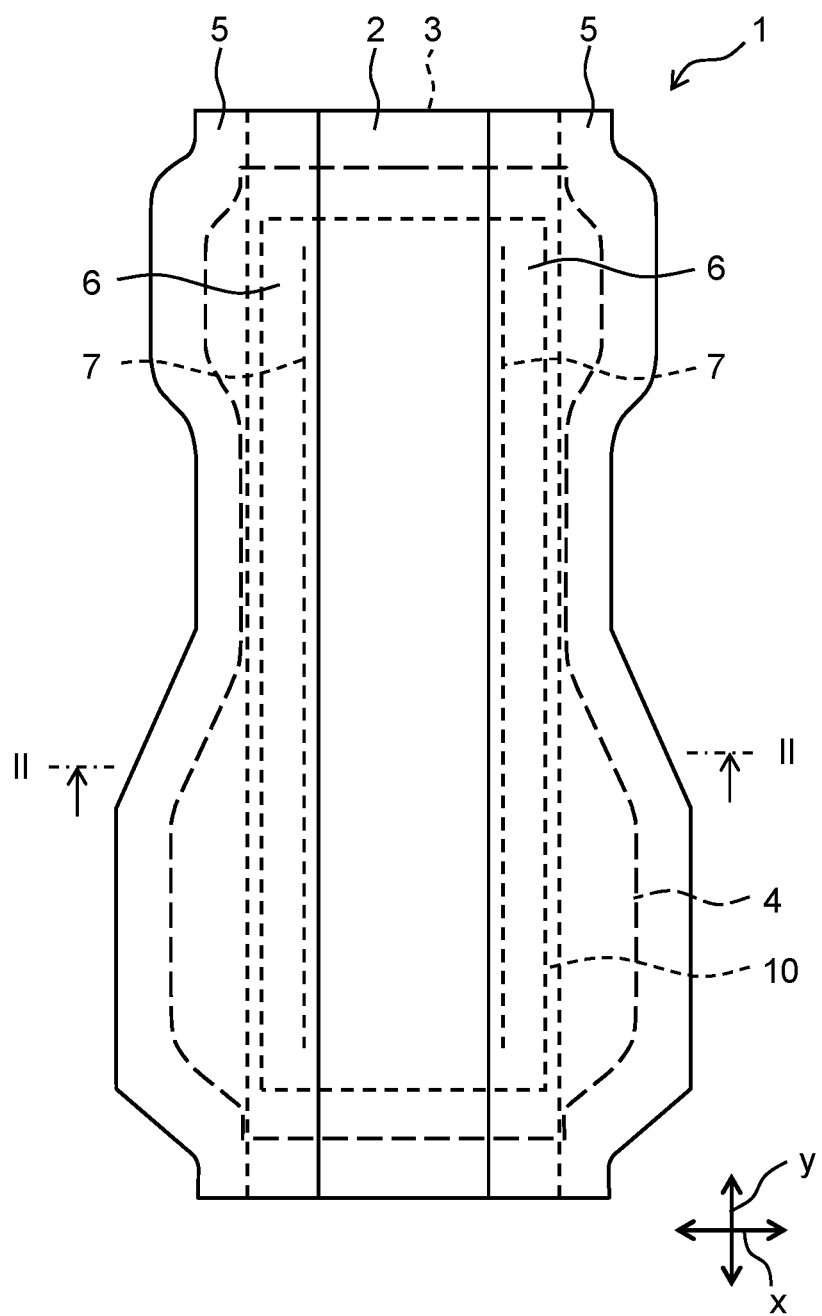
FIG. 1 shows a plan view of an incontinence pad seen from a top sheet side, as an absorbent article of the present invention.

An absorbent article of the present invention comprise a top sheet, a back sheet and an absorbent body disposed therebetween, and further comprises a second sheet disposed between the top sheet and the absorbent body. The absorbent article of the present invention can be applied to, for example, a disposable diaper, an incontinence pad (including a light incontinence pad), a sanitary napkin and the like.

The absorbent article has a longitudinal direction and a width direction. The longitudinal direction means a direction extending in a front-rear direction at a crotch of a wearer when the wearer wears the absorbent article. The width direction means a direction orthogonal to the longitudinal direction on the same plane as the absorbent article, and corresponds to a left-right direction of the wearer in wearing the absorbent article. In addition, a plane direction means a direction parallel to the plane formed from the longitudinal direction and the width direction, and a thickness direction means a direction orthogonal to that.

A shape of the absorbent article is not particularly limited. In the case that the absorbent article is an incontinence pad or a sanitary napkin, examples of the shape of the absorbent article include a substantially rectangular shape, an oval shape, an hourglass shape, a center nipped-in gourd shape and others.

In the case that the absorbent article is a disposable diaper, a disposable diaper has, for example, a front part, a rear part, and a crotch part positioned therebetween and provided with an absorbent body. The disposable diaper may comprise, for example, a pants member having a front part, a rear part and a crotch part positioned therebetween, and a laminate comprising a top sheet, a back sheet and an absorbent body disposed therebetween, wherein the laminate is provided at the crotch part. The disposable diaper may be formed such that a laminate comprising a top sheet, a back sheet and an absorbent body disposed therebetween is formed in a pants shape having a front part, a rear part and a crotch part positioned therebetween.

The front part is a part applied to an abdomen side of a wearer, the rear part is a part applied to a back side of the wearer in wearing the disposable diaper. The crotch part is a part positioned between the front part and the rear part and applied to a crotch of the wearer.

The disposable diaper may be an open-type (tape-type) disposable diaper that is provided with a pair of fastening members on left and right ends of the rear part and is formed into a pants shape by using the fastening members in wearing, or the disposable diaper may be a pants-type disposable diaper that has a waist opening and a pair of leg openings formed by joining the front part and the rear part to each other.

The top sheet is a sheet which is located on a wearer's side in wearing the absorbent article and preferably liquid-permeable. As the top sheet, a nonwoven fabric made from hydrophilic fibers such as cellulose, rayon and cotton; and a nonwoven fabric which is formed from hydrophobic fibers such as polyolefin (e.g., polypropylene, polyethylene), polyester (e.g., PET) and polyamide (e.g., nylon), and in which the hydrophobic fibers are hydrophilized with a surfactant on the surface thereof; can be used, for example. As the top sheet, a woven fabric, a knitted fabric, a plastic film having holes may be also used.

The back sheet is a sheet which is located on an opposite side of a wearer, that is an exterior side, in wearing the absorbent article and preferably liquid-impermeable. As the back sheet, a nonwoven fabric made from hydrophobic fibers such as polyolefin (e.g., polypropylene, polyethylene), polyester (e.g., PET) and polyamide (e.g., nylon), and a plastic film, can be used, for example. As the back sheet, a laminate of a nonwoven fabric and a plastic film may be also used. In the present invention, the meaning of "liquid-impermeable" includes water-repellent.

In the case of using a nonwoven fabric as the top sheet or the back sheet, a spunbonded nonwoven fabric, a point-bonded nonwoven fabric, an air-through nonwoven fabric, a meltblown nonwoven fabric, an airlaid nonwoven fabric, a spunlace nonwoven fabric, an SMS nonwoven fabric or the like is preferably used as the nonwoven fabric.

The absorbent body is not particularly restricted as long as it contains an absorbent material which is able to absorb excrement such as urine. As the absorbent body, a shaped product of an absorbent material, which is formed into a predefined shape, may be used, or the shaped product wrapped with a covering sheet such as a paper (e.g., a tissue paper and a thin paper) and a liquid-permeable nonwoven fabric may be used. Examples of the absorbent material include, for example, a hydrophilic fiber such as a pulp fiber and an absorbent polymer such as a polyacrylic absorbent polymer, a polyasparaginic absorbent polymer, a cellulosic absorbent polymer, and a stark-acrylonitrile absorbent polymer. The absorbent material may include a thermal fusion fiber such as a polyolefin (e.g., polyethylene and polypropylene) fiber, a polyester (e.g., PET) fiber and a polyamide fiber. These thermal fusion fibers may be hydrophilized with a surfactant or the like to increase affinity with urine and the like.

The absorbent material preferably includes a hydrophilic fiber in view of increasing absorption rate of urine and the like. In addition, in view of enhancing absorption capacity, the absorbent material preferably includes an absorbent polymer. Therefore, the absorbent body preferably contains both a hydrophilic fiber (especially a pulp fiber) and an absorbent polymer. In this case, the absorbent material is preferably formed by mixing an absorbent polymer with a hydrophilic fiber assembly, or dispersing an absorbent polymer on a hydrophilic fiber assembly, for example.

The absorbent body may be a sheet-shaped absorbent body. Examples of the sheet-shaped absorbent body include an object which is formed to contain an absorbent polymer but not contain a pulp fiber between nonwoven fabrics. The sheet-shaped absorbent body formed in this manner enables high absorption capacity since it contains an absorbent polymer between nonwoven fabrics. In addition, since the sheet-shaped absorbent body does not contain a pulp fiber between nonwoven fabrics, it can be formed thin without being bulky.

For the sheet-shaped absorbent body, an absorbent fiber may be used as the absorbent material. Also in this case, the sheet-shaped absorbent body is formed thin without being bulky. Examples of the absorbent fiber include a fiber having a protonated carboxyl group or a carboxylate group. The absorbent fiber can be obtained by, for example, hydrolyzing an acrylic fiber, thereby converting a nitrile group contained in the acrylic fiber to a carboxylic group, as disclosed in Japanese Examined Patent Application Publication No. S52-42916. The carboxyl group contained in the absorbent fiber preferably forms an alkaline metal salt or an ammonium salt. The absorbent fiber also can be prepared by immersing a hydrophilic fiber in acrylic acid to deposit acrylic acid on the surface of the fiber.

A shape (planar shape) of the absorbent body is not particularly limited. The shape of the absorbent body is determined as appropriate according to application, and examples of the shape of the absorbent body include a substantially rectangular shape, an hourglass shape, a center nipped-in gourd shape, a battledore shape and others.

The second sheet is a sheet that is disposed between the top sheet and the absorbent body. In the present invention, the second sheet is composed of a laminate having a nonwoven fabric layer and a plastic film layer from the top sheet side and has a plurality of through-holes. That is, the second sheet is formed by laminating a nonwoven fabric layer and a plastic film layer to be integrated, and the nonwoven fabric layer is disposed so as to be positioned on the top sheet side, the plastic film layer is disposed so as to be positioned on the back sheet side, and a plurality of holes are formed so as to penetrate the second sheet from a surface of the top sheet side to a surface of the back sheet side.

In the absorbent article of the present invention, since the second sheet formed in the above manner is disposed between the top sheet and the absorbent body, urine and the like excreted from a wearer and permeated through the top sheet can be rapidly drawn into the absorbent body, and wettability of the top sheet can be reduced. Thus, since the nonwoven fabric layer is present on the surface of the second sheet at the top sheet side, urine and the like absorbed by the top sheet is rapidly transferred to the second sheet by capillary effect of the nonwoven fabric layer and urine and the like which has reached the second sheet further passes through the second sheet through the thorough-holes formed in the second sheet to transfer to the absorbent body. Meanwhile, urine and the like which has reached the absorbent body is prevented from returning to the top sheet side by the presence of the plastic film layer of the second sheet. Therefore, the absorbent article of the present invention comes to be excellent in absorbing performance of urine and the like and is capable of reducing wettability of the top sheet, thereby improving a wearing feeling.

A kind of a nonwoven fabric constituting the nonwoven fabric layer is not particularly limited, however, it is preferably hydrophilic. As the nonwoven fabric constituting the nonwoven fabric layer, nonwoven fabrics available for the top sheet can be used. The nonwoven fabric constituting the nonwoven fabric layer is preferably formed from a thermal fusion fiber such as polyolefin (e.g., polypropylene, polyethylene), polyester (e.g., PET), polyamide (e.g., nylon), whereby it becomes easy to form embossed parts on the nonwoven fabric by heat-embossing, as described later. Constituent fibers of the nonwoven fabric may be composed of a single component or may be composed of multi-component (i.e. a composite fiber).

Examples of the nonwoven fabric constituting the nonwoven fabric layer includes, for example, a point-bonded nonwoven fabric, an air-through nonwoven fabric, a spun-bonded nonwoven fabric, a meltblown nonwoven fabric, an airlaid nonwoven fabric, a spunlace nonwoven fabric and the like. From the aspect of enhancing the drawing force of urine and the like from the top sheet, it is preferred that an adhesive is not used for interfiber bonding of the nonwoven fabric constituting the nonwoven fabric layer, and a nonwoven fabric whose fibers are joined or interlaced together by heating (including self-fusion) or water flow is preferably used. Therefore, the nonwoven fabric layer is preferably made of a point-bonded nonwoven fabric, an air-through nonwoven fabric, a spunbonded nonwoven fabric, a meltblown nonwoven fabric or a spunlace nonwoven fabric layer. Further, from the viewpoint of enhancing the drawing force of urine and the like, it is preferred that voids between fibers of the nonwoven fabric layer are made some large; and therefore, the nonwoven fabric layer is preferably made of a point-bonded nonwoven fabric, an air-through nonwoven fabric, a spunbonded nonwoven fabric or a spunlace nonwoven fabric layer.

The nonwoven fabric layer is preferably made of a heat-embossed nonwoven fabric. When the nonwoven fabric constituting the nonwoven fabric layer is heat-embossed, volume of the nonwoven fabric layer is suppressed, whereby a remaining amount of urine and the like in the nonwoven fabric layer can be reduced, while ensuring the drawing effect of urine and the like by the nonwoven fabric layer. Therefore, the amount of urine and the like that returns to the top sheet from the second sheet can be decreased.

A kind of the heat-embossed nonwoven fabric is not particularly limited; and for example, a point-bonded nonwoven fabric is formed by thermal-compressing (heat-embossing) a thermal fusion short-fiber web with an embossing roll, whereby the fibers are joined together to be formed into a nonwoven fabric, and therefore, the heat-embossed nonwoven fabric can be obtained easily by employing a point-bonded nonwoven fabric. A spunbonded nonwoven fabric is formed by collecting melt-spun continuous fibers on a conveyor belt to form a web and thermal-compressing with an embossing roll, whereby the fibers are joined together to be formed into a nonwoven fabric, and also by employing a spunbonded nonwoven fabric, the heat-embossed nonwoven fabric can be easily obtained. Of course, the heat-embossed nonwoven fabric may be obtained by heat-embossing a nonwoven fabric which was not embossed in manufacturing. However, from the viewpoint of easily manufacturing, a point-bonded nonwoven fabric or a spunbonded nonwoven fabric is preferably used for the nonwoven fabric layer as the heat-embossed nonwoven fabric.

A shape and arrangement of the embossed parts formed by the heat-embossing is not particularly limited, and the embossed parts are preferably disposed in a scattered pattern in any shape. Each single shape of the embossed parts is not particularly limited and may be a circular shape, an elliptical shape, an oval shape, a polygonal shape, a wavy shape, a starlike shape or the other; and these may be disposed in a regular pattern or in a random pattern. In the case where the embossed parts are disposed in a regular pattern, the embossed parts are preferably disposed at lattice points of any lattice. Each of the embossed parts preferably has an area of $0.05$ $mm^2$ to $10$ $mm^2$ and the embossed parts are preferably arranged such that an average distance between adjacent embossed parts is 0.5 mm to 10 mm. The shape and arrangement of the embossed parts described herein shall be defined in a state where the through hole is not formed.

The nonwoven fabric layer is preferably made of a short-fiber nonwoven fabric. When the nonwoven fabric layer is made of a short-fiber nonwoven fabric, urine or the like which has reached the nonwoven fabric layer of the second sheet tends to promptly transfer to the absorbent body through the through-holes. For example, in the case where the nonwoven fabric layer is made of a long-fiber nonwoven fabric, urine and the like tends to spread widely along a fiber orientation direction of the long-fibers in the nonwoven fabric layer, and as a result, urine and the like tends to slowly transfer to the absorbent body from the second sheet. In addition, as a result of widely spreading of urine and the like in the nonwoven fabric layer, urine and the like tends to remain over a wide area in the second sheet where the through-holes are not formed, and there is possibility to increase a returning amount of urine and the like to the top sheet. However, when the nonwoven fabric layer is made of a short-fiber nonwoven fabric, spreading of urine and the like in the planar direction is suppressed as compared with the case of using a long-fiber nonwoven fabric; and as a result, a larger amount of urine and the like easily transfer to the absorbent body from the second sheet via the through-holes, whereby the effect of reducing wettability of the top sheet can be improved.

In the case where the nonwoven fabric layer is made of a short-fiber nonwoven fabric, it is preferred that the constituent fibers of the nonwoven fabric orient in the longitudinal direction of the absorbent article. When the nonwoven fabric layer is constituted in this manner, the effect of reducing wettability of the top sheet can be enhanced and the whole of the absorbent body tends to contribute to the absorption of urine and the like effectively, since in the nonwoven fabric layer, urine and the like spreads more easily in the longitudinal direction than in the width direction of the absorbent article. Further, also in the case where the nonwoven fabric layer is made of a long-fiber nonwoven fabric, it is preferred that the constituent fibers of the nonwoven fabric orient in the longitudinal direction.

Therefore, it is particularly preferable that the nonwoven fabric layer is made of a point-bonded nonwoven fabric, and the constituent fibers of the point-bonded nonwoven fabric preferably orient in the longitudinal direction of the absorbent article.

As the plastic film layer, a film formed from a resin such as polyolefin (e.g., polypropylene, polyethylene), polyester (e.g., PET), polyamide (e.g., nylon) can be used. The plastic film layer is preferably hydrophobic, however, it may be hydrophilized by surfactant or the like. It is preferred that the plastic film layer is not embossed, whereby the plastic film layer is less likely to be ruptured.

The plastic film layer is disposed on the back sheet side of the nonwoven fabric layer and is laminated to the nonwoven fabric layer to be integrated. The nonwoven fabric layer and the plastic film layer is preferably joined to each other with an adhesive, whereby rupture strength of the plastic film layer is likely to be ensured as compared with, for example, the case where the nonwoven fabric layer and the plastic film layer are thermal-bonded to each other. In addition, the plastic film layer is prevented from heat-hardening and flexibility of the second sheet can be ensured. The nonwoven fabric layer and the plastic film layer are preferably joined to each other by an adhesive which is entirely coated, whereby urine and the like tends to be prevented from remaining between the nonwoven fabric layer and the plastic film layer.

A method of forming the through-holes is not particularly limited, as long as the through-holes are formed so as to penetrate the laminate of the nonwoven fabric layer and the plastic film layer. The through-holes may be formed by boring with a needle or a convex mold or by punching with a cutting die in the laminate of the nonwoven fabric layer and the plastic film layer. Or, the through-holes may be formed by burning with a laser or blowing high-pressure air to the laminate of the nonwoven fabric layer and the plastic film layer. The through-holes are preferably formed in large numbers all over the second sheet.

A shape (planar shape) of the through-hole is not particularly limited and is preferably formed in a shape that is longer in the longitudinal direction of the absorbent article. Examples of the shape of the through-hole include a circular shape, an elliptical shape, an oval shape, a polygonal shape, a dumbbell shape and others. When the through-hole is formed in a shape that is longer in the longitudinal direction of the absorbent article, urine and the like spreads more easily in the longitudinal direction than in the width direction in the second sheet and the whole of the absorbent body is likely to contribute to the absorption of urine and the like, effectively.

Each of the through-holes is preferably formed larger than the embossed-parts formed by heat-embossing. When the through-holes are formed larger than the embossed parts, urine and the like easily moves to the through-hole without remaining at the embossed part and further easily moves to the absorbent body through the through-hole. An area of each of the through-holes may be about $0.1$ $mm^2$ to $10$ $mm^2$. Further, the second sheet is preferably formed such that a total area of the through-holes is larger than that of the embossed parts in a certain area (for example, an area of 5 cm×5 cm), whereby urine and the like easily transfers to the absorbent body through the through-holes.

In the second sheet, it is preferred that the nonwoven fabric layer is intruded into the through-hole. That is, in the second sheet, it is preferred that the nonwoven fabric is into the through-hole of the plastic film layer. When the through-hole is formed in this manner, an inner surface of the through-hole is covered with the nonwoven fabric also in the plastic film layer, and therefore, urine and the like is likely to smoothly move to the through-holes from the nonwoven fabric layer. As a result, urine and the like easily moves to the absorbent body through the through-holes smoothly, whereby wettability of the top sheet can be further reduced.

It is preferred that a surface of the back sheet side of the second sheet projects toward the back sheet along an outer edge of the through-hole. When the second sheet is formed in this manner, urine and the like which has passed through the through-hole tends to smoothly move to the absorbent body by running down the part projecting toward the back sheet along the outer edge of the through-hole. As a result, wettability of the top sheet can be further reduced.

Examples of a method of forming the above-described through-hole in the second seat include a method of inserting a needle or a convex mold into a laminate of the nonwoven fabric layer and the plastic film layer from the nonwoven fabric layer side to make a hole. By forming the through-hole in this manner, the second sheet formed in such that the nonwoven fabric layer is intruded into the through-hole and a surface of the back sheet side of the second sheet projects toward the back sheet along the outer edge of the through-hole can be easily obtained.

The second sheet is preferably provided adjacent to the top sheet. In addition, the second seat is preferably provided adjacent to the absorbent body. Further, the second sheet is preferably formed to be narrower in the width direction and the longitudinal direction than the absorbent body.

In the case where the second sheet is provided adjacent to the top sheet, the second sheet is preferably joined and fixed to the top sheet, thereby improving structural stability of the absorbent article. In this case, it is preferred that the second sheet is joined to the top sheet with an adhesive from the viewpoint of easy production of the absorbent article.

In the case that the top sheet and second sheet are joined to each other with an adhesive, it is preferred that the top sheet and second sheet are joined to each other with an adhesive applied in a line. Examples of an applying pattern of the adhesive include, for example, a straight linear patter, a meandering linear pattern and a spiral pattern. When the top sheet and the second sheet are joined to each other in this manner, urine and the like which has passed through the top sheet is likely to transfer to the second sheet smoothly.

The top sheet is preferably made of a heat-embossed nonwoven fabric. When the top sheet is made of a heat-embossed nonwoven fabric, the top sheet is made relatively thin, and hence, urine and the like is likely to promptly pass through the top sheet and is less likely to remain in the top sheet. Therefore, it becomes possible to reduce wettability of the top sheet. In addition, by heat-embossing the nonwoven fabric constituting the top sheet, fluffing of fibers constituting the nonwoven fabric is suppressed and texture thereof can be improved. As the heat-embossed nonwoven fabric, heat-embossed nonwoven fabrics available for the above-described nonwoven fabric layer of the second sheet may be used. A shape and arrangement of the embossed parts formed by heat-embossing are also referred to the above description. Preferably, the top sheet is made of a point-bonded nonwoven fabric or a spunbonded nonwoven fabric.

The top sheet is preferably made of a long-fiber nonwoven fabric. In the absorbent article of the present invention, it becomes possible that urine and the like which has passed through the top sheet is promptly drawn into the absorbent body by the presence of the second sheet. Meanwhile, from the viewpoint of reducing wettability of the top sheet, it is preferable that diffusivity of urine and the like in the second sheet is not so high. Therefore, in order to ensure the diffusivity in the planar direction in the absorbent article as a whole, it is preferred that the top sheet is made of a long-fiber nonwoven fabric, thereby enhancing the diffusivity of urine and the like in the top sheet. When the top sheet is made of a long-fiber nonwoven fabric, urine and the like easily spreads along a fiber orientation direction of the long-fibers in the top sheet, and the diffusivity of urine and the like in the planar direction can be ensured in the absorbent article as a whole. In the case where the top sheet is made of a long-fiber nonwoven fabric, it is preferred that the constituent fibers of the nonwoven fabric orient in the longitudinal direction of the absorbent article, whereby the whole of the absorbent body is likely to effectively contribute to the absorption of urine and the like. Therefore, it is particularly preferable that the top sheet is made of a spunbonded nonwoven fabric.

It is preferred that the nonwoven fabric layer of the second sheet has a lower mass per a unit area than the top sheet. In the absorbent article of the present invention, urine and the like can be prevented from returning to the top sheet side by the presence of the second sheet; however, there is possibility that some of the urine and the like remaining on the nonwoven fabric layer of the second sheet returns to the top sheet by being compressed by the wearer. In spite of that, when the nonwoven fabric layer of the second sheet is formed to have a lower mass per a unit area than the top sheet, the returning amount can be suppressed as compared with water-holding capacity of the top sheet even in the case where urine and the like remaining in the nonwoven fabric layer of the second sheet returns to the top sheet, whereby it becomes possible to maintain the top sheet to be relatively dry.

Figure 2:
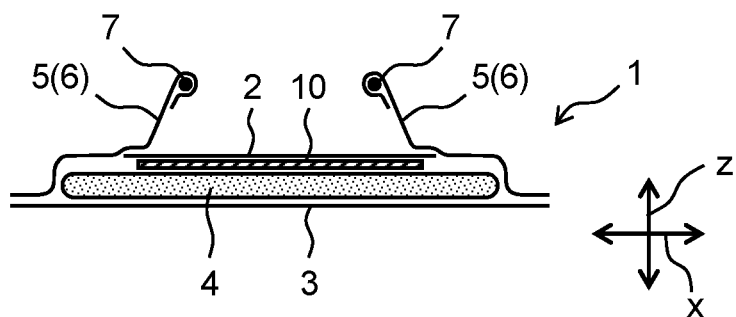
FIG. 2 shows a cross-sectional view along a line II-II of the absorbent article shown in FIG. 1.
Figure 3:
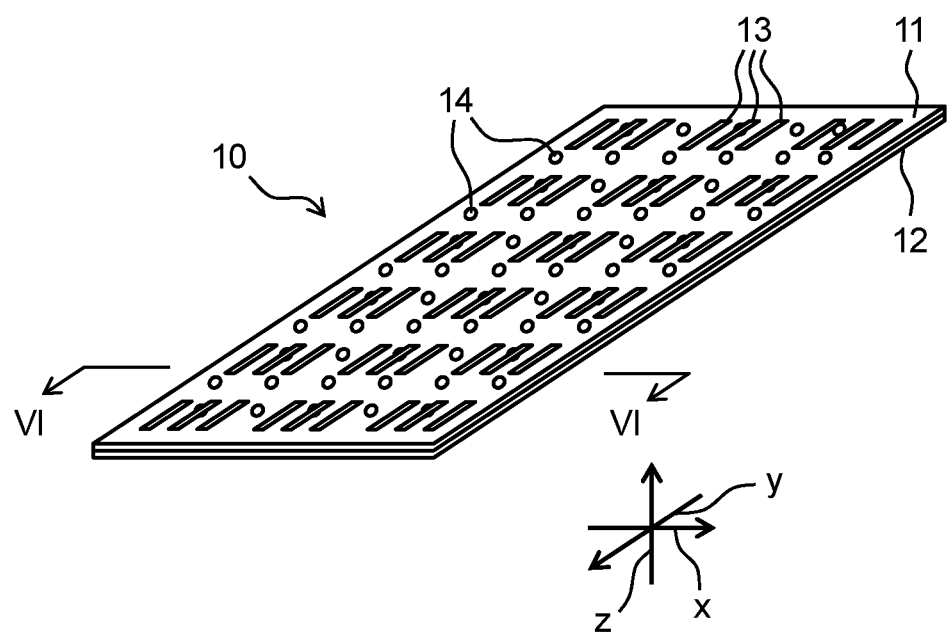
FIG. 3 shows an enlarged perspective view of a second sheet of the absorbent article shown in FIGS. 1 and 2.
Figure 4:
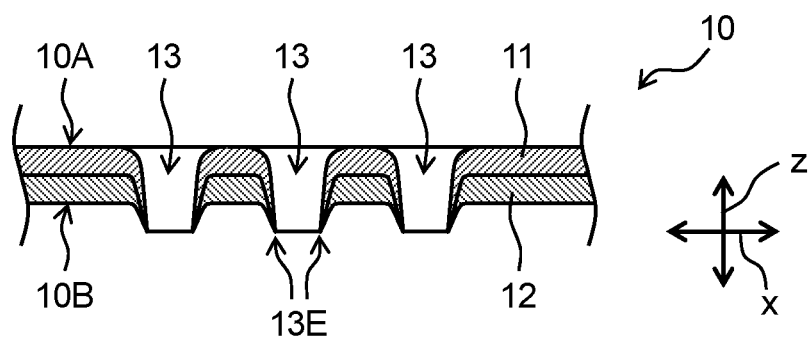
FIG. 4 shows a cross-sectional view along a line VI-VI of the second sheet shown in FIG. 3.

Next, an example of the absorbent article of the present invention is explained with an incontinence pad, referring to FIGS. 1 to 4. FIG. 1 shows a plan view of an incontinence pad seen from a top sheet side, as an example of the absorbent article of the present invention. FIG. 2 shows a cross-sectional view along a line II-II of the absorbent article shown in FIG. 1. FIG. 3 shows an enlarged perspective view of a second sheet of the absorbent article shown in FIGS. 1 and 2. FIG. 4 shows a cross-sectional view along a line VI-VI of the second sheet shown in FIG. 3. In the drawings, an arrow x represents the width direction and an arrow y represents the longitudinal direction, and an arrows z represents a thickness direction. However, the present invention is not limited to the embodiment shown in the drawings.

An absorbent article 1 comprises a top sheet 2, a back sheet 3 and an absorbent body 4 therebetween, and further comprises a second sheet 10 between the top sheet 2 and the absorbent body 4. The top sheet 2 is provided so as to face skin of a crotch of a wearer and allows liquid excrement such as urine permeate. The excrement such as urine which has passed through the top sheet 2 transfers to the absorbent body 4 via the second sheet 10 and is accommodated in the absorbent body 4. The back sheet 3 prevents excrement from leaking outside.

A pair of side sheets 5 extending in the longitudinal direction y are provided on both sides of the top sheet 2 in the width direction x. The side sheet 5 is joined to the top sheet 2 and is provided with a rising elastic member 7 at an inner end part thereof in the width direction x. The inner end part of the side sheet 5 rises toward wearer's skin by contractive force of the rising elastic member 7, thereby forming a rising flap 6 that prevents leakage of excrement such as urine.

The second sheet 10 is composed of a laminate having a nonwoven fabric layer 11 and a plastic film layer 12 from the top sheet 2 side and has a plurality of through-holes 13 (refer to FIGS. 3 and 4). Since the absorbent article 1 is provided with the second sheet 10 formed in this manner, urine and the like absorbed by the top sheet 2 is promptly drawn into the second sheet 10 by the nonwoven fabric layer 11, and further the urine and the like which has reached the second sheet 10 can transfer to the absorbent body 4 through the through-holes 13. Meanwhile, urine and the like which has transferred to the absorbent body 4 is prevented from returning to the top sheet 2 side by the presence of the plastic film layer 12. Therefore, the absorbent article 1 comes to be excellent in absorbing performance of urine and the like, and wettability of the top sheet 2 is reduced to improve a wearing feeling.

The nonwoven fabric layer 11 is made of a nonwoven fabric which has embossed parts 14 formed by heat-embossing. In FIG. 3, a plurality of the embossed parts 14 are aligned in the longitudinal direction y and the width direction x. When the nonwoven fabric layer 11 is made of a heat-embossed nonwoven fabric, volume of the nonwoven fabric layer 11 is suppressed, whereby a remaining amount of urine and the like in the nonwoven fabric layer 11 can be reduced, while the effect of drawing urine and the like by the nonwoven fabric layer 11 is ensured. Therefore, it is possible to reduce a returning amount of urine and the like to the top sheet 2.

The second sheet 10 is preferably formed such that the nonwoven fabric layer 11 is intruded into the through-holes 13 as shown in FIG. 4. When the through-hole 13 is formed in this manner, urine and the like tends to smoothly move to the through-hole 13 via nonwoven fabric layer 11. In FIG. 3, each of the through-holes 13 is formed in a rectangular shape that is longer in the longitudinal direction y, and a plurality of the through-holes 13 are aligned in the longitudinal direction y and the width direction x.

A surface 10B of the back sheet side of the second sheet 10 projects toward the back sheet along an outer edge 13E of the through-hole 13, whereby urine and the like which has passed through the through-hole 13 tends to smoothly move to the absorbent body 4 by running down the part projecting toward the back sheet along the outer edge 13E of the through-hole 13. Meanwhile, a surface 10A of the top sheet side of the second sheet 10 is preferably formed to be inclined toward both the center of the through-hole 13 and the back sheet at the outer edge 13E of the through-hole 13, whereby urine and the like easily moves to the through-hole 13 smoothly.

This application claims priority to Japanese Patent Application No. 2014-144278, filed on Jul. 14, 2014, the entire contents of which are incorporated by reference herein.

REFERENCE SIGNS LIST

1: an absorbent article (an incontinence pad)
2: a top sheet
3: a back sheet
4: an absorbent body
10: a second sheet
11: a nonwoven fabric layer
12: a plastic film layer
13: a through-hole
14: an embossed part

The invention claimed is:

1. An absorbent article comprising a top sheet, a back sheet, an absorbent body disposed therebetween and a second sheet disposed between the top sheet and the absorbent body, wherein
the second sheet is composed of a laminate having a nonwoven fabric layer and a plastic film layer, the nonwoven fabric layer being closer to the top sheet than the plastic film layer,
the nonwoven fabric layer is made of a point-bonded nonwoven fabric that is formed by heat-embossing a thermal fusion short-fiber web with an embossing roll to be formed into a nonwoven fabric and that is formed with a plurality of embossed parts,
the second sheet has a plurality of through-holes that extend into the nonwoven fabric layer and the plastic film layer, and
each of the through-holes extending into the nonwoven fabric layer is larger than the plurality of embossed parts formed on the point-bonded nonwoven fabric.

2. The absorbent article according to claim 1, wherein each of the through-holes has an area of 0.1 mm$^2$ to 10 mm$^2$.

3. The absorbent article according to claim 1, wherein each of the plurality of through-holes is formed in a shape that is longer in a longitudinal direction of the absorbent article.

4. The absorbent article according to claim 1, wherein a total area of the through-holes is larger than that of the embossed parts in an area of 5 cm×5 cm of the second sheet.

5. The absorbent article according to claim 1, wherein the nonwoven fabric layer is intruded into each of the plurality of through-holes.

6. The absorbent article according to claim 1, wherein a surface of the back sheet side of the second sheet projects toward the back sheet along an outer edge of the through-hole.

7. The absorbent article according to claim 1, wherein the nonwoven fabric layer is made of a short-fiber nonwoven fabric and constituent fibers of the short-fiber nonwoven fabric orient in a longitudinal direction of the absorbent article.

8. The absorbent article according to claim 1, wherein the nonwoven fabric layer and the plastic film layer are joined to each other with an adhesive.

9. The absorbent article according to claim 1, wherein the nonwoven fabric layer has a lower mass per a unit area than the top sheet.

10. The absorbent article according to claim 1, wherein the top sheet is made of a heat-embossed nonwoven fabric.

11. The absorbent article according to claim 1, wherein the top sheet is made of a point-bonded nonwoven fabric or a spunbonded nonwoven fabric.

12. The absorbent article according to claim 11, wherein the top sheet is made of a spunbonded nonwoven fabric and constituent fibers of the spunbonded nonwoven fabric orient in the longitudinal direction of the absorbent article.

13. The absorbent article according to claim 1, wherein the top sheet and the second sheet are joined to each other with an adhesive applied in a line.

14. The absorbent article according to claim 1,
wherein the plurality of embossed parts are formed on the nonwoven fabric layer of the second sheet at positions where the first plurality of through-holes are not formed.

15. The absorbent article according to claim 1, wherein each of the plurality of through-holes have an area of 0.1 mm² to 10 mm², and each of the plurality of embossed parts have an area of 0.05 mm² to 10 mm².

16. The absorbent article according to claim 1, wherein the plurality of the embossed parts have a different shape from the plurality of the through-holes.

17. The absorbent article according to claim 1, wherein the plastic film layer is not embossed.

\* \* \* \* \*